(12) United States Patent
Pappas et al.

(10) Patent No.: US 9,872,826 B2
(45) Date of Patent: Jan. 23, 2018

(54) MANUFACTURING PROCESSES FOR GELLAN GUM-BASED FLUID GELS

(71) Applicant: Colgate-Palmolive Company, New York, NY (US)

(72) Inventors: Iraklis Pappas, Pennsauken, NJ (US); Jason Nesta, Cedar Knolls, NJ (US); Shira Pilch, Highland Park, NJ (US)

(73) Assignee: Colgate-Palmolive Company, New York, NY (US)

( * ) Notice: Subject to any disclaimer, the term of this patent is extended or adjusted under 35 U.S.C. 154(b) by 174 days.

(21) Appl. No.: 14/648,359

(22) PCT Filed: Dec. 3, 2012

(86) PCT No.: PCT/US2012/067541
§ 371 (c)(1),
(2) Date: May 29, 2015

(87) PCT Pub. No.: WO2014/088534
PCT Pub. Date: Jun. 12, 2014

(65) Prior Publication Data
US 2015/0297491 A1    Oct. 22, 2015

(51) Int. Cl.
| | | |
|---|---|---|
| *A61K 8/73* | (2006.01) | |
| *A61K 8/20* | (2006.01) | |
| *A61Q 11/00* | (2006.01) | |
| *A61K 8/04* | (2006.01) | |
| *C08B 37/00* | (2006.01) | |
| *C08J 3/075* | (2006.01) | |
| *C08L 5/00* | (2006.01) | |
| *C08J 3/24* | (2006.01) | |

(52) U.S. Cl.
CPC ............... *A61K 8/73* (2013.01); *A61K 8/042* (2013.01); *A61K 8/20* (2013.01); *A61Q 11/00* (2013.01); *C08B 37/006* (2013.01); *C08J 3/075* (2013.01); *C08J 3/24* (2013.01); *C08L 5/00* (2013.01); *C08J 2305/00* (2013.01)

(58) Field of Classification Search
USPC ............... 426/573; 204/469; 521/50
See application file for complete search history.

(56) References Cited

U.S. PATENT DOCUMENTS

| | | | | |
|---|---|---|---|---|
| 4,876,105 | A | * | 10/1989 | Wolf .............. C08L 89/06 426/573 |
| 2004/0168920 | A1 | | 9/2004 | Thorne et al. |
| 2005/0137272 | A1 | | 6/2005 | Gaserod et al. |
| 2009/0068259 | A1 | | 3/2009 | Pilch et al. |
| 2009/0269288 | A1 | | 10/2009 | Lavrova |
| 2013/0272970 | A1 | | 10/2013 | Pimenta et al. |
| 2013/0272971 | A1 | | 10/2013 | Pimenta et al. |
| 2013/0280181 | A1 | | 10/2013 | Nesta et al. |

FOREIGN PATENT DOCUMENTS

| | | |
|---|---|---|
| CN | 1313755 | 9/2001 |
| CN | 101795730 | 8/2010 |
| CN | 101824095 | 9/2010 |
| GB | 2384705 | 8/2003 |
| JP | H10-291928 | 11/1998 |
| JP | H11-15502 | 1/1999 |
| JP | 2004-298061 | 10/2004 |
| JP | 2007-222035 | 9/2007 |
| JP | 2009-011270 | 1/2009 |
| WO | WO 12/087326 | 6/2012 |

OTHER PUBLICATIONS

Mao, R. et al., "Gelling Temperatures of Gellan Solutions as Affected by Citrate Buffers," Journam of Food Science, 1999, vol. 64, No. 4, pp. 648-652.
Mao, Runsheng et al., "Effect of pH Buffers on Mechanical Properties of Gellan Gels," Journal of Texture Studies, 1999, vol. 30, No. 2, pp. 151-166.
Corresponding Chinese Office Action dated Mar. 16, 2016.
Cpkelco, A Huber Company, 2005, Kelcogel® Gellan Gum Book, 5th ed., www.cpkelco.com.
Franco Picone et al., 2010, "Influence of pH on formation and properties of gellan gels," Carbohydrate Polymers 84(1):662-668.
International Search Report and Written Opinion in International Application PCT/US2012/067541, dated Sep. 30, 2013.
Morris et al., 2012, "Gelation of gellan—A Review," Food Hydrocolloids 28:373-411.
Ogawa et al., 2002, "Conformational transition of gellan gun of sodium, litiuin, and postassium types in aqueous solutions," Food Hydrocolloids 16(1):1-9.
Written Opinion in International Application PCT/US2012/067541, dated Dec. 4, 2014.
Wu Li-jun et al., 2005, "Factors Affecting Rheological Property of Gellan Gum Aqueous Solution," Beverage & Fast Frozen Food Industry 11(3):9-15.

* cited by examiner

Primary Examiner — Walter Webb

(57) ABSTRACT

Disclosed is a method of manufacturing a fluid gel, the method comprising adding metal cations to the gellant dispersion while retaining the pH at no greater than 3; and adding a pH modifying agent to the gellant dispersion to increase the pH of the gellant dispersion to greater than 3.

23 Claims, No Drawings

MANUFACTURING PROCESSES FOR GELLAN GUM-BASED FLUID GELS

BACKGROUND

The rheology of fluid gels containing low acyl gellan gum is notoriously dependent on the processing conditions under which the fluid gel is formed. The efficacy of the processing conditions typically has a profound impact on the bulk properties of the final gelled system.

The critical stage in the processing of gellan gum occurs when gellan polymer strands crosslink to form an extended molecular network. Crosslinking can be determined by simple inspection of the structure of low acyl gellan gum. The repeating tetrasaccharide backbone contains a glucuronic acid residue, and the carboxyl group on this residue can share cations with adjacent gellan strands, leading to weak coordinate bonds bridging multiple strands, causing crosslinking which provides the extended molecular network.

Furthermore, crosslinking can be controlled by adjusting the temperature of the solution: above a certain temperature, sometimes referred to as the gelation temperature, crosslinking will not occur.

One typical known processing scheme of gellan gum includes the following steps: heat a solution of gellan gum to an elevated temperature above the gelation temperature to avoid crosslinking; then add crosslinking cations and allow complete dissolution of gellan gum and the cations, the elevated temperature being sufficiently high to ensure such complete dissolution; and then cool the solution below the gelation temperature to cause crosslinking This known process allows all crosslinking cations to distribute uniformly throughout the solution before gelation, and allows the exact moment of gelation to be controlled.

However, this approach is not desirable because of the energy required during the heating and cooling cycle.

Those skilled in the art of producing such gels know that rapid or immediate crosslinking is undesirable, because such rapid crosslinking prevents uniform distribution of the cations. This in turn leads to a system with heterogeneous rheology due to localized highly-crosslinked domains, and gel domains with low crosslinking.

There is accordingly a need in the art for a method of manufacturing a gel comprising gellan gum which has lower energy consumption than known manufacturing methods and can consistently provide homogeneous rheological properties in the gel.

There is also a need in the art for a method of manufacturing a gel comprising gellan gum which has a reduced processing time and energy consumption as compared to known manufacturing methods.

SUMMARY

One aim of this invention is to provide a method of manufacturing a gel comprising gellan gum which has lower energy consumption than known manufacturing methods and can consistently provide homogeneous rheological properties in the gel.

Another aim of this invention is to provide a method of manufacturing a gel comprising gellan gum which has a reduced processing time and energy consumption as compared to known manufacturing methods.

According to one aspect of this invention, there is provided a method of manufacturing a fluid gel, the method comprising the steps of:

(a) adding metal cations to the gellant dispersion while retaining the pH at no greater than 3; and
(b) adding a pH modifying agent to the gellant dispersion to increase the pH of the gellant dispersion to greater than 3.

In some embodiments, the addition of the metal cations to the gellant dispersion causes the metal cations to cross-link the gellan gum in the gellant dispersion.

Optionally, in step (a) the metal cations are selected from alkali metal cations or alkali earth metal cations, or a mixture thereof.

Optionally, in step (a) the metal cations are selected from sodium, potassium, calcium or magnesium cations, or a mixture thereof. Typically, in step (a) the metal cations comprise sodium cations, more typically in step (a) the metal cations being comprised in sodium chloride.

Optionally, steps (a) and (b) are carried out at substantially the same temperature. Optionally, steps (a) and (b) are carried out at a temperature of less than 35° C. Typically, steps (a) and (b) are carried out at a temperature of from 15 to 30° C., more typically at a temperature of from 20 to 25° C.

Optionally, the gellant dispersion comprises gellan gum in an amount of from 0.05 to 2 wt % based on the weight of the gellant dispersion. Typically, the gellant dispersion comprises gellan gum in an amount of from 0.05 to 0.5 wt % based on the weight of the gellant dispersion. More typically, the gellant dispersion comprises gellan gum in an amount of from 0.075 to 0.125 wt % based on the weight of the gellant dispersion.

Optionally, in step (a) the metal cations are added to the gellant dispersion to provide a metal cation concentration of 0.05 to 2M in the gellant dispersion. Typically, in step (a) the metal cations are added to the gellant dispersion to provide a metal cation concentration of from 0.05 to 0.5M in the gellant dispersion. More typically, in step (a) the metal cations are added to the gellant dispersion to provide a metal cation concentration of from 0.75 to 0.125M in the gellant dispersion.

Optionally, in step (a) the metal cations are added to the gellant dispersion to provide a metal cation concentration of from 0.1 to 0.5 wt % based on the weight of the gellant dispersion. Further optionally, in step (a) the metal cations are added to the gellant dispersion to provide a metal cation concentration of from 0.15 to 0.35 wt % based on the weight of the gellant dispersion. Yet further optionally, in step (a) the metal cations are added to the gellant dispersion to provide a metal cation concentration of from 0.2 to 0.3 wt % based on the weight of the gellant dispersion.

Optionally, the gellant dispersion is produced by dispersing the gellan gum in water until the gellan gum is substantially fully hydrated and then adding an acid to reduce the pH of the gellant dispersion to a pH value of no greater than 3. Typically, the acid is phosphoric acid. Typically, the gellan gum is substantially fully dissolved in the aqueous medium.

Optionally, the gellan gum is a low acyl gellan gum.

Optionally, in step (b) the pH is increased to a value of at least 3.5.

The present invention further provides a method of manufacturing a mouthwash composition including cross-linked gellan gum as a structuring agent, the method comprising the steps of:

i. providing a gellant dispersion including cross-linked gellan gum produced according to the method of the invention; and
ii. combining the cross-linked gellan gum with at least one other mouthwash ingredient.

The present invention further provides a cross-linked gellant gum manufactured by the method of the invention.

The present invention further provides a mouthwash composition including cross-linked gellan gum according to the invention as a structuring agent or manufactured according to the method of the invention.

The mouthwash composition manufactured according to the invention may contain additional therapeutic and non-therapeutic components as known to those skilled in the art.

This invention is predicated on the finding by the present inventors that by controlling the pH of a gellan gel dispersion, the initiation of a crosslinking can be reliably and accurately controlled, so that a fluid gel may be produced which has uniform and consistent rheology as a result of substantially homogeneous crosslinking of the gellan gum.

An initial low pH composition avoids crosslinking of the gellan gum, even when metal cations are present as potential crosslinking components, and subsequently increasing the pH above a threshold triggers crosslinking. The crosslinking can be reliably prevented, and then reliably triggered, by pH control without requiring any additional temperature control, in particular any heating above, or cooling below, the gel temperature of the gellan gum dispersion. By avoiding such temperature control relative to the gelling temperature of the gellan gum, the energy consumption of the manufacturing process can be reduced, and the batch processing time can also be reduced, while ensuring homogeneous cross-linking by the pH control.

The fluid gel produced in accordance with the embodiments of the invention have particular application in the manufacture of mouthwash compositions.

In a mouthwash composition, the pH should be above pH=3.5, otherwise the composition is too acidic for use in the oral cavity as a mouthwash. Thus, it is not possible to create a structured mouthwash using low acyl gellan gum which is only crosslinked with $H^+$. Using the crosslinking process for gellan gum described herein, the final pH can be any value above pH=3. Furthermore, the gelation process is less dependent on the mixing efficiency or metal salt addition. Utilizing this manufacturing process presents significant advantages in batch cycle time reduction and energy consumption reduction for mouthwash manufacture.

In this specification, the term "structural parameter" is used to indicate the ratio of the elastic modulus (G') to the viscous modulus (G"), as is known in the art. The structural parameter defines the rheological properties of a viscoelastic material. If the structural parameter is greater than 1, the rheological properties are primarily elastic, and a fluid gel having such a high structural parameter is highly structured. If the structural parameter is less than 1, the rheological properties are primarily viscous, and a fluid gel having such a low structural parameter has low structure.

The invention provides a manufacturing process which can consistently control the structural parameter of a fluid gel containing crosslinked gellan gum as a structurant, in which the structural parameter of the crosslinked gellan gum is greater than 1, the rheological properties are primarily elastic, and the fluid gel is highly structured. The gellan gum may optionally be employed in combination with other structurants.

DETAILED DESCRIPTION

It should be understood that the detailed description and specific examples, while indicating embodiments of the invention, are intended for purposes of illustration only and are not intended to limit the scope of the invention.

As referred to herein, all compositional percentages are by weight of the total composition, unless otherwise specified.

The invention disclosed herein includes a method of manufacturing a fluid gel, the method comprising the steps of: (a) adding metal cations to the gellant dispersion while retaining the pH at no greater than 3; and (b) increasing the pH of the gellant dispersion to greater than 3.

In some embodiments, adding the metal cations to the gellant dispersion causes the metal cations to cross-link the gellan gum in the gellant dispersion.

Typically, the gellan gum is a low acyl gellan gum. Typical low acyl gellan gums suitable for use in the present invention are available commercially from the company CP Kelco under the trade names Kelcogel CG-LA, Kelcogel, Kelcogel F, and Kelcogel AFT.

As used herein, the term "low acyl" gellan gum refers to a gellan gum wherein the glucose residues do not contain any acyl groups (e.g. acetate or glycerate), as opposed to gellan gums which in their native or "high acyl" form possess two acyl substituents—acetate and glycerate—on the same glucose residue; and on average, contain one glycerate per repeat and one acetate per every two repeats.

The low acyl gellan gum has a particular ability to produce a low-viscosity suspension in products such as mouthwash. The suspension can suspend active components or particulate material, for active and/or aesthetic effects. The metal cations interact with the low acyl gellan gum to give a fluid gel, which is a low viscosity liquid having an appreciable yield stress.

Optionally, the gellant dispersion comprises gellan gum in an amount of from 0.05 to 2 wt % based on the weight of the gellant dispersion. Typically, the gellant dispersion comprises gellan gum in an amount of from 0.05 to 0.5 wt % based on the weight of the gellant dispersion. More typically, the gellant dispersion comprises gellan gum in an amount of from 0.075 to 0.125 wt % based on the weight of the gellant dispersion.

Optionally, the gellant dispersion is produced by dispersing the gellan gum in water until the gellan gum is substantially fully hydrated and then adding an acid to reduce the pH of the gellant dispersion to a pH value of no greater than 3. Typically, the acid is phosphoric acid. However, any other orally compatible inorganic or organic acid or mixture of any of such acids may be used as a pH adjuster. Typically, the gellan gum is substantially fully dissolved in the aqueous medium.

In some embodiments, in step (a) the metal cations are selected from alkali metal cations or alkali earth metal cations, or a mixture thereof, and typically are selected from sodium, potassium, calcium or magnesium cations, or a mixture thereof. In a particular embodiment the metal cations comprise sodium cations, more typically being comprised in sodium chloride, as a salt added to the dispersion.

Optionally, in step (a) the metal cations are added to the gellant dispersion to provide a metal cation concentration of 0.05 to 2M in the gellant dispersion. Typically, in step (a) the metal cations are added to the gellant dispersion to provide a metal cation concentration of from 0.05 to 0.5M in the gellant dispersion. More typically, in step (a) the metal cations are added to the gellant dispersion to provide a metal cation concentration of from 0.75 to 0.125M in the gellant dispersion.

Optionally, in step (a) the metal cations are added to the gellant dispersion to provide a metal cation concentration of from 0.1 to 0.5 wt % based on the weight of the gellant dispersion. Further optionally, in step (a) the metal cations are added to the gellant dispersion to provide a metal cation concentration of from 0.15 to 0.35 wt % based on the weight of the gellant dispersion. Yet further optionally, in step (a) the metal cations are added to the gellant dispersion to provide a metal cation concentration of from 0.2 to 0.3 wt % based on the weight of the gellant dispersion.

Optionally, in step (b) the pH is increased to a value of at least 3.5.

In some embodiments, steps (a) and (b) are carried out at substantially the same temperature; there is no subsequent heating or cooling of the gellant gum dispersion provided in step (a). Optionally, steps (a) and (b) are carried out at a temperature of less than 35° C. Typically, steps (a) and (b) are carried out at a temperature of from 15 to 30° C., more typically at a temperature of from 20 to 25° C.

Some embodiments of the invention therefore provide a method of processing low acyl gellan gum which does not require a heating/cooling cycle, but which prevents the premature onset of gelation caused by the addition of metal cations. The inventors have discovered that, by adjusting the pH of the low acyl gellan gum solution prior to the addition of the metal cations, it is possible to prevent the metal cations from crosslinking the gum. Thus, the metal cations can be uniformly dissolved in solution before crosslinking occurs. Following adequate dissolution, crosslinking by the metal cations can be triggered by a second adjustment of the solution pH. This procedure is especially useful in manufacturing environments where mixing efficiency is poor. It is also particularly useful when the salts must be added in solid form instead of as a liquid premix.

The present invention further provides a method of manufacturing a mouthwash composition including cross-linked gellan gum as a structuring agent, the method comprising the steps of:
  i. providing a gellant dispersion including cross-linked gellan gum produced according to the method of the invention; and
  ii. combining the cross-linked gellan gum with at least one other mouthwash ingredient.

The present invention further provides a mouthwash composition including cross-linked gellan gum according to the invention as a structuring agent or manufactured according to the method of the invention.

The mouthwash composition manufactured according to the invention may contain additional therapeutic and non-therapeutic components as known to those skilled in the art.

The fluid gel including gellan gum used in accordance with the invention is structured to provide a structured composition having desired rheological properties for the desired use, for example for use as a mouthwash.

The structured composition may optionally comprise additional structurants, thickeners, emulsifiers and/or stabilizers. For example, the structured composition may additionally include at least one gum such as guar gum, which may be raw, chemically unmodified or chemically modified. Alternatively or additionally, the structured composition may additionally include at least one cellulose polymer, which may be present as a salt, for example the sodium salt. Optionally, the at least one cellulose polymer is selected from one or more of hydroxypropylmethyl cellulose (HPMC), hydroxyethylpropyl cellulose (HEPC), hydroxybutylmethyl cellulose (HBMC), and carboxymethyl cellulose (CMC). In some embodiments, the at least one cellulose polymer comprises a mixture of cellulose materials having different molecular weight.

The mouthwash composition manufactured according to the method of the invention may be administered to or applied to a human or other animal subject. The composition is suitable for administration or application to the oral cavity of a human or animal subject.

The following examples further describe and demonstrate illustrative embodiments within the scope of the present invention. The examples are given solely for illustration and are not to be construed as limitations of this invention as many variations are possible without departing from the spirit and scope thereof. Various modifications of the invention in addition to those shown and described herein should be apparent to those skilled in the art and are intended to fall within the appended claims.

EXAMPLES

Comparative Example 1

In Comparative Example 1, a fluid gel composed of gellan gum was prepared and the structural parameter was measured at different pH values.

The following preparation procedure was used: 1 g of low acyl gellan gum was dissolved in 1 of deionized (DI) water yielding a 0.1 wt % solution of low acyl gellan gum. The mixture was stirred gently for 3 hours in order to ensure complete hydration of the gellan gum. The temperature of the solution was 25° C.

After hydration, an appropriate amount of 85 wt % phosphoric acid ($H_3PO_4$) was added to the stirred solution in order to reduce the pH to a respective preset pH value as specified in Table 1. In other words, eight samples of the gellan gum solution were provided, and each sample was adjusted in pH to the respective preset value indicated in Table 1, namely 1.0, 1.5, 2.0, 2.5, 3.0, 3.5, 4.0 and 4.5. The temperature of the solution during the PH adjusting step was 25° C.

The structural parameter of each sample was measured using an oscillatory strain sweep experiment, which was carried out using a TA AR-G2 rheometer outfitted with a serrated cup-and-bob geometry. The experiment was run at a frequency of 1 Hz and a temperature of 25° C. The structural parameter was recorded at a strain of 1%.

For the fluid gel of Comparative Example 1, this strain was within the linear viscoelastic region.

An aliquot of this pH-adjusted solution for each sample was loaded into the rheometer and the structural parameter was measured. The structural parameter for each sample is shown in Table 1. The temperature of the solution during the rheology measurement was 25° C.

Above pH=3, the structural parameter is less than 1. Below pH=3, a dramatic increase in the structural parameter is observed. As the pH is decreased further, the structural parameter reduces.

Without being bound by any theory, it is believed that this phenomenon can be considered as a direct result of the glucuronic acid residue. The pKa of glucuronic acid in low acyl gellan gum is approximately 3.5. When the pH is near or above this pKa, glucuronic acid is largely deprotonated and strands of low acyl gellan gum repel each other. There is no crosslinking and thus the structural parameter is less than 1. When the pH is lower than the pKa, partial protonation occurs and strands of low acyl gellan gum begin to share $H^+$. This sharing (crosslinking) is accompanied by a dramatic increase in the structural parameter. When the pH is much lower than the pKa, more complete protonation of glucuronic acid occurs and the extent of $H^+$ sharing decreases—corresponding to a reduction in the structural parameter.

Example 1

In Example 1, a fluid gel composed of gellan gum was prepared as for Comparative Example 1 and then eight samples of the fluid gel were provide, each being pH-adjusted to a respective corresponding pH value as for the samples of Comparative Example 1. However, additionally a metal cation was added to the pH-adjusted samples, each sample having a common metal ion molar concentration, prior to measuring the structural parameter of the samples having the different pH values.

The same preparation procedure was used as for Comparative Example 1 to produce a 0.1 wt % solution of low acyl gellan gum, and with complete hydration of the gellan gum. As for Comparative Example 1, after hydration, an appropriate amount of 85 wt % phosphoric acid ($H_3PO_4$) was added to the stirred solution in order to reduce the pH to a respective preset pH value as specified in Table 1. In other words, eight samples of the gellan gum solution were provided, and each sample was adjusted in pH to the respective preset value indicated in Table 1, namely 1.0, 1.5, 2.0, 2.5, 3.0, 3.5, 4.0 and 4.5.

Next, crystalline NaCl was added to each sample of the rapidly stirring pH-adjusted solution to achieve a final NaCl concentration, and metal cation molar concentration, of 100 mM in each of the eight samples.

During each step, the temperature of the solution was 25° C.

An aliquot of each sample of this NaCl-adjusted and pH adjusted solution was loaded into the rheometer and the structural parameter was measured, using the same technique, apparatus and parameters as for Comparative Example 1. The structural parameter for each sample is also shown in Table 1.

With respect to the samples of the pH-adjusted low acyl gellan gum solutions after addition of NaCl, the data described in Table 1 demonstrates that in the range of pH=3 to pH=4.5, the structural parameter is essentially unchanged as compared to the pH-adjusted low acyl gellan gum solution without addition of NaCl.

Without being bound by any theory, it is believed that over the pH=3 to pH=4.5 pH regime, all $Na^+$ cations are participating in crosslinking. As the pH is lowered below pH=3, the structural parameter successively decreases, mirroring the behavior for Comparative Example 1. In this low-pH regime, protonation of glucuronic acid prevents $Na^+$ cations from participating in crosslinking.

It is therefore apparent that the addition of NaCl has no significant impact on structural parameter when the pH is below pH=3. Thus, NaCl which is added to an acidified low acyl gellan gum solution does not contribute to crosslinking. By subsequently increasing the pH above pH=3, the $H^+$ concentration is decreased and $Na^+$ becomes the sole cross-linking cation.

Accordingly, in accordance with embodiments of the invention, an acidified low acyl gellan gum solution can be provided with metal cations, but the low pH prevents the metal cations from participating in crosslinking the gellan gum. Then when the pH is raised subsequently, the metal cations then do participate in crosslinking the gellan gum, providing a structured fluid gel with a high structural parameter. The pH can be readily controlled uniformly throughout the composition, which in turn provides a homogeneously crosslinked fluid gel with consistent rheology. No temperature change relative to the gel temperature is required, and the crosslinking can be achieved at a constant temperature.

TABLE 1

Structural Parameter vs. pH

| pH | Comparative Example 1 Structural Parameter G'/G" (No NaCl added) | Example 1 Structural Parameter G'/G" (100 mM NaCl) |
|---|---|---|
| 1.0 | 2.35 | 3.08 |
| 1.5 | 3.37 | 3.9 |
| 2.0 | 5.85 | 4.85 |
| 2.5 | 6.39 | 6.26 |
| 3.0 | 0.24 | 7.03 |
| 3.5 | 0.38 | 6.7 |
| 4.0 | 0.32 | 6.63 |
| 4.5 | 0.35 | 6.84 |

The invention claimed is:

1. A method of manufacturing a fluid gel, the method comprising the steps of:
   (a) adding metal cations to a gellant dispersion having a pH of no greater than 3 while retaining the pH of said dispersion at no greater than 3; and
   (b) adding a pH modifying agent to the gellant dispersion to increase the pH of the gellant dispersion to greater than 3,
wherein steps (a) and (b) are carried out at a temperature of less than 35° C.

2. The method according to claim 1, wherein the addition of the metal cations to the gellant dispersion causes the metal cations to cross-link the gellan gum in the gellant dispersion.

3. The method according to claim 1 wherein in step (a) the metal cations are selected from alkali metal cations or alkali earth metal cations, or a mixture thereof.

4. The method according to claim 3 wherein in step (a) the metal cations are selected from sodium, potassium, calcium or magnesium cations, or a mixture thereof.

5. The method according to claim 4 wherein in step (a) the metal cations comprise sodium cations.

6. The method according to claim 5 wherein in step (a) the metal cations are comprised in sodium chloride.

7. The method according to claim 1 wherein steps (a) and (b) are carried out at substantially the same temperature.

8. The method according to claim 1 wherein steps (a) and (b) are carried out at a temperature of from 15 to 30° C.

9. The method according to claim 8 wherein steps (a) and (b) are carried out at a temperature of from 20 to 25° C.

10. The method according to claim 1 wherein the gellant dispersion comprises gellan gum in an amount of from 0.05 to 2 wt % based on the weight of the gellant dispersion.

11. The method according to claim 10 wherein the gellant dispersion comprises gellan gum in an amount of from 0.05 to 0.5 wt % based on the weight of the gellant dispersion.

12. The method according to claim 11 wherein the gellant dispersion comprises gellan gum in an amount of from 0.075 to 0.125 wt % based on the weight of the gellant dispersion.

13. The method according to claim 1 wherein in step (a) the metal cations are added to the gellant dispersion to provide a metal cation concentration of 0.05 to 2M in the gellant dispersion.

14. The method according to claim 13 wherein in step (a) the metal cations are added to the gellant dispersion to provide a metal cation concentration of from 0.05 to 0.5M in the gellant dispersion.

15. The method according to claim 14 wherein in step (a) the metal cations are added to the gellant dispersion to provide a metal cation concentration of from 0.75 to 0.125M in the gellant dispersion.

16. The method according to claim 1 wherein in step (a) the metal cations are added to the gellant dispersion to provide a metal cation concentration of from 0.1 to 0.5 wt % based on the weight of the gellant dispersion.

17. The method according to claim 16 wherein in step (a) the metal cations are added to the gellant dispersion to provide a metal cation concentration of from 0.15 to 0.35 wt % based on the weight of the gellant dispersion.

18. The method according to claim 17 wherein in step (a) the metal cations are added to the gellant dispersion to provide a metal cation concentration of from 0.2 to 0.3 wt % based on the weight of the gellant dispersion.

19. The method according to claim 1 wherein the gellant dispersion is produced by dispersing the gellan gum in water until the gellan gum is substantially fully hydrated and then adding an acid to reduce the pH of the gellant dispersion to a pH value of no greater than 3.

20. The method according to claim 19 wherein the acid is phosphoric acid.

21. The method according to claim 19 wherein the gellan gum is substantially fully dissolved in the aqueous medium.

22. The method according to claim 1, wherein the gellan gum is a low acyl gellan gum.

23. The method according to claim 1 wherein in step (b) the pH is increased to a value of at least 3.5.

* * * * *